United States Patent
Partsky

[11] Patent Number: 5,988,870
[45] Date of Patent: Nov. 23, 1999

[54] APPARATUS AND METHOD FOR DILUTING NASAL SPRAYS CONTAINING ADDICTIVE COMPOUNDS

[76] Inventor: Howard Partsky, 34 Farm to Market Rd., Brewster, N.Y. 10509

[21] Appl. No.: 09/033,252
[22] Filed: Mar. 2, 1998
[51] Int. Cl.⁶ .................. B01F 3/00; B65D 1/32
[52] U.S. Cl. .......... 366/348; 366/143; 366/130; 604/212; 239/327
[58] Field of Search ............... 366/143, 348, 366/129, 130; 604/207, 217, 212, 246, 251, 260, 37; 215/3; 222/1, 206; 239/1, 327, 318

[56] References Cited

U.S. PATENT DOCUMENTS

| | | |
|---|---|---|
| 53,790 | 4/1866 | Curtiss, Jr. ................. 215/3 |
| 2,564,400 | 8/1951 | Hall ........................ 239/327 |
| 3,140,052 | 7/1964 | McCuiston ............... 239/327 |
| 4,564,129 | 1/1986 | Urban et al. ............ 239/327 |

*Primary Examiner*—Tony G. Soohoo
*Attorney, Agent, or Firm*—Arthur L. Plevy

[57] ABSTRACT

An apparatus and method capable of diluting nasal sprays containing addictive compounds. The user can safely and gradually withdraw from use of nasal sprays with successive dilutions using the apparatus having at least one indicia and a pre-selected level on the container. The spray is administered by the user using the method by depleting the nasal spray to the pre-selected level and replenishing with a diluent. The method steps are repeated until the concentration of the nasal spray is substantially reduced.

20 Claims, 1 Drawing Sheet

APPARATUS AND METHOD FOR DILUTING NASAL SPRAYS CONTAINING ADDICTIVE COMPOUNDS

BACKGROUND OF THE INVENTION

1. Field of the Invention

This invention relates to an apparatus and method for diluting nasal sprays containing addictive compounds which substantially reduces the strength of the spray.

2. Description of Related Art

Millions of people suffer from the symptoms of the common cold or other sinus-related problems, such as sinusitis and hay fever. Included among these symptoms is "rhinitis," a medical term for blocked or clogged sinuses. Seeking relief from these symptoms, symptomatic persons use nasal decongestants which are available over-the-counter without a prescription. The most popular of these decongestants contain oxymetazoline or a pharmaceutically acceptable salt thereof. Other nasal preparations available over-the-counter contain compounds such as xylometazoline, naphazoline, phenylephrine and pharmaceutically acceptable salts thereof.

Nasal decongestants containing oxymetazoline, for example, offer fast and effective relief from nasal congestion. Unfortunately, oxymetazoline has undesired side-effects, one of which includes addiction if used beyond the recommended dosage period. Since many people who use nasal sprays remain symptomatic beyond the recommended dosage period, and despite warnings that the spray should not be used for more than three or four days, usage generally continues beyond the dosage period. Thus, a person using the spray in an effort to seek relief from their continued symptoms will subsequently become addicted.

Addiction or habitual overuse of nasal spray has a long and documented history in medical literature. "Rhinitis Medicamentosa" used in identifying the addiction or habitual overuse is discussed in a 1994 article from the Department of Otorhinolaryngology at Söder Hospital, Karolinska Institute, Stockholm, Sweden, entitled "Overuse of Oxy- and Xylometazoline Nasal Sprays" by Peter Graf.

As described in the article, a compensatory vasodilation remains after the vasocontrictive effects of the drug have disappeared. The pathophysiology of this "rebound" swelling caused by use of nasal spray is not known. After repeated use, a person will find that their sinuses become clogged due to this "rebound" reaction to the spray. This leads a person to use the nasal spray repeatedly, causing increasing congestion. In time, the spray becomes increasingly less effective to the user. Alleviating this rebound swelling altogether requires that the use of the nasal spray be ceased.

One approach in treating the problem is immediate cessation, or stopping "cold turkey." This type of withdrawal is very difficult for people addicted to the habit, as it causes extreme discomfort. Other approaches in treating the problem include prescribing topical steroid nasal inhalers or oral systemic steroids which have a multitude of undesired side effects. Relief from congestion in many cases takes days or weeks and often sedatives are needed to help with the resulting insomnia.

U.S. Pat. Nos. 4,970,240 and 5,114,979 describe an aqueous topical nasal decongestant containing oxymetazoline or a salt thereof to which a fruity flavor is added to mask the aftertaste of the composition. No provision is made for assisting the user in withdrawing from addiction to these compositions.

Methods and compositions for treating addiction to drugs, alcohol, and tobacco, such as those described in U.S. Pat. Nos. 5,272,149; 5,219,858; 5,198,230; 4,496,545; 3,885,027; 4,582,705; 4,500,515; 4,596,825; 5,656,255; 5,688,804; and 5,594,030 are of possible general interest.

For those who are unable to stop using nasal sprays completely, there remains a need for a device and method which is easy to use and effective for the withdrawal from addictive use of nasal sprays without the need for immediate cessation or steroids and accompanying side effects.

SUMMARY OF THE INVENTION

Briefly described, the invention comprises an apparatus and method for diluting nasal sprays containing addictive compounds which substantially reduces the concentration of the addictive compound in the spray and accordingly reduces the addiction or habitual overuse of these compounds.

The apparatus comprises a container holding a volume of nasal spray having at least one indicia at a pre-selected level on the container. The indicia is a mark, sign, or symbol signifying the level to which the nasal spray must be depleted prior to adding a diluent. One example of an indicia is a horizontal line around the circumference of the container. The apparatus has a second indicia showing the initial volume of the spray in the container. The level to which the nasal spray is depleted is selected according to the needs of the user, since the severity of symptoms, mucosal swelling, and addiction to the spray is directly proportional to the frequency and dosage strength used. Generally, an indicia indicating 15% of the initial total volume is selected. When the user wishes to withdraw more rapidly from using the spray, a greater percentage of initial total volume will be removed.

Once the level is selected, the spray can either be administered or removed to the pre-selected level and discarded. Means are provided for depleting the nasal spray, such as an applicator nozzle or a removable top. The depleted volume of the nasal spray is replenished with a diluent, such as sodium chloride solution. Sodium chloride is employed as a diluting agent because it provides a soothing, moisturizing, and therapeutic effect. Diluent can be added to the nasal spray using an eye dropper, syringe, or other similar device.

The method comprises the successive dilution of the nasal spray using an apparatus having indicia at a pre-selected level. The nasal spray is depleted to the pre-selected level and replenished with a diluent, such as sodium chloride solution. Alternatively. distilled water is employed as a diluent. Selecting a level to which the spray is depleted depends on the needs of the user, but generally the indicia is located at the level showing 15% from the total initial volume. The steps of the method are repeated until the concentration of the nasal spray is substantially reduced, and the user can withdraw from use of the spray without needless suffering. Optimally, the user can repeat the steps approximately thirty times, until the solution primarily consists of diluent.

These and other features of the invention will be more fully understood by reference to the following drawings.

DETAILED DESCRIPTION OF THE INVENTION

During the course of this description, like numbers will be used to identify like elements according to the different views that illustrate the invention.

Figure 1:
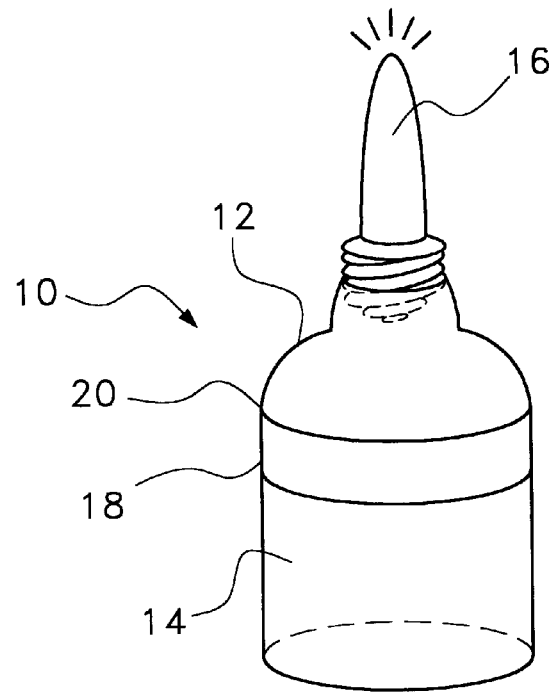
FIG. 1 is a perspective view of the apparatus shown with two indicia.

The preferred embodiment of the invention 10 is illustrated in FIG. 1. The container 12 contains nasal spray 14 and is covered by a screw-off spray top 16. The container 12 is either a bottle for nasal solution or a plastic squeeze bottle for nasal spray. The top 16 is easily removable to allow access to the solution 14 at specific intervals when the diluent is added. The nasal spray 14 contains 0.05% oxymetazoline hydrochloride, but can contain other formulations containing addictive compounds known in the art.

The container 12 has a first indicia 18 and a second indicia 20 around the periphery. First indicia 18 is preferably located at the level showing 15% depletion of the total initial volume of the spray 14. Second indicia 20 is located at the level showing the initial total volume of the spray 14. Initially, the person using the system will use the spray 14 at the normal dosage, and the level of fluid will fall below the second indicia 20. When the level of the nasal spray 14 reaches the first indicia 18, the user is prompted to add diluent. The user can then either add sodium chloride solution, or distilled water as diluent. Preferably, sodium chloride 0.065% solution is employed. Diluent can be added by way of an eye dropper or syringe, being careful not to contaminate the nasal spray 14. Diluent is added until the level reaches the second indicia 20. The second indicia 20 aids the user when replenishing the depleted amount of nasal spray with a diluent. At this point, the concentration of the spray 14 is reduced by a factor of 15%. This procedure is repeated approximately 30 times or until the concentration of the nasal spray 14 is substantially reduced.

How quickly the solution needs dilution is determined completely by how often the person uses the medication and the amount used with each administration. This invention provides flexibility in allowing for comfortable and individualized withdrawal from addiction or habitual overuse to nasal spray. The gradual and comfortable withdrawal will help make the attempt to quit successful.

Optionally, a "fast track" approach is possible with the present invention. Under this approach, a person would not wait until the spray 14 is depleted to the first indicia 18. The container 12 can be emptied to the level of the first indicia 18, by either administration or disposal. The diluent can then be added on a daily basis, as opposed to an "as needed" or consumption basis, and therefore, the attempt to quit is placed on a "fast track."

The reductions in concentration provided by the invention are as follows:

| DAY | % STRENGTH |
|---|---|
| 1 | 100.00 |
| 2 | 85.0 |
| 3 | 72.25 |
| 4 | 61.41 |
| 5 | 52.20 |
| 6 | 44.37 |
| 7 | 37.71 |
| 8 | 32.05 |
| 9 | 27.24 |
| 10 | 23.15 |
| 11 | 19.68 |
| 12 | 16.73 |
| 13 | 14.22 |
| 14 | 12.09 |
| 15 | 10.28 |
| 16 | 8.74 |
| 17 | 7.43 |
| 18 | 6.32 |
| 19 | 5.37 |
| 20 | 4.56 |
| 21 | 3.88 |
| 22 | 3.30 |
| 23 | 2.81 |
| 24 | 2.39 |
| 25 | 2.03 |
| 26 | 1.73 |
| 27 | 1.47 |
| 28 | 1.25 |
| 29 | 1.06 |
| 30 | 0.90 |

This "fast track" approach provides a pre-determined 30-day withdrawal method. Under the "fast track" method, a person should be able to completely stop using the system and be free of addiction at the end of thirty days.

Figure 2:
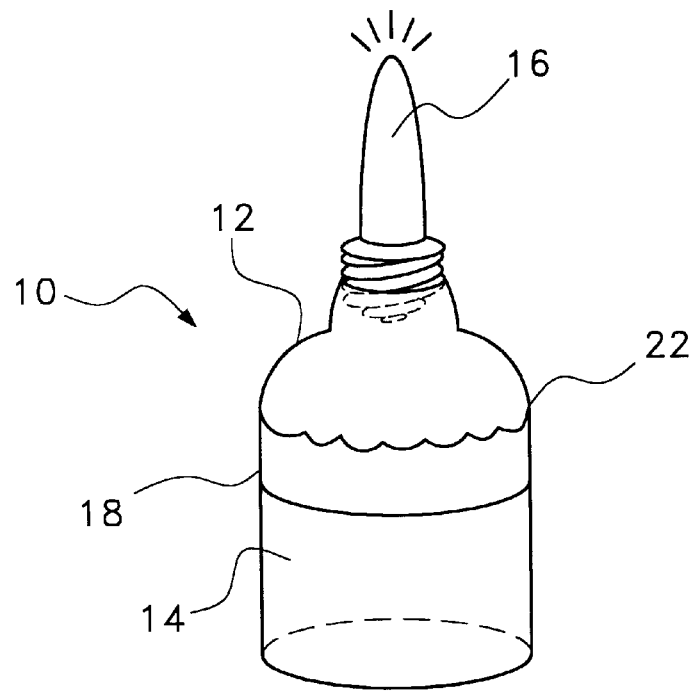
FIG. 2 is a perspective view of the apparatus shown with one indicia.

FIG. 2 shows an alternate embodiment of the invention. One indicia 18 is shown on the container. Presumably, a user would know the initial level 22 of the spray prior to use. The indicia 18 indicates the level at which the diluent should be added. The user can employ the procedures outlined above in the preferred embodiment when using the alternate embodiment of the invention.

While the invention has been described with reference to the preferred embodiment thereof, it will be appreciated by those of ordinary skill in the art that modifications can be made to the parts that comprise the invention without departing from the spirit and scope thereof.

What is claimed is:

1. A method for diluting a nasal spray containing addictive compounds, comprising the steps of:
   providing a container for holding an initial volume of nasal spray with indicia at a pre-selected level;
   depleting an amount of spray to the pre-selected level;
   replenishing the depleted amount with diluent; and
   repeating the steps of depleting and replenishing until the strength of said spray is substantially reduced.

2. The method according to claim 1, wherein said indicia comprises a first horizontal line around the circumference of said container.

3. The method according to claim 2, wherein said indicia further comprises a second horizontal line around the circumference of said container indicating initial volume.

4. The method according to claim 3, wherein said diluent comprises sodium chloride solution.

5. The method according to claim 4, wherein said addictive compound comprises oxymetazoline or a pharmaceutically acceptable salt thereof.

6. The method according to claim 3, wherein said diluent comprises distilled water.

7. The method according to claim 6, wherein said steps of depleting and replenishing are repeated approximately 30 times.

8. A method for gradually diluting a nasal spray containing addictive compounds, comprising the steps of:
   providing a bottle for containing nasal spray with means for indicating a level where a selective amount of the initial volume of spray in said bottle is to be depleted;
   depleting the volume of said spray by said selective amount;

adding diluent to said bottle until the initial volume is reached; and repeating the steps of depleting and adding until the concentration of said spray is substantially reduced.

9. The method according to claim 8, wherein said means for indicating comprises a first horizontal line around the circumference of said bottle.

10. The method according to claim 9, wherein said means for indicating further comprises a second horizontal line around the circumference of said bottle indicating initial volume.

11. The method according to claim 10, wherein said selective amount is approximately 15%.

12. The method according to claim 11, wherein said diluent comprises sodium chloride solution.

13. The method according to claim 12, wherein said addictive compound comprises oxymetazoline or pharmaceutically acceptable salt thereof.

14. The method according to claim 13, wherein the steps of depleting and adding are repeated approximately 30 times.

15. The method according to claim 11, wherein said diluent comprises distilled water.

16. An apparatus capable of diluting a nasal spray containing addictive compounds, comprising:

a container with a volume of nasal spray at an initial level;

at least one indicia at a pre-selected level on said container;

means for depleting said nasal spray; and means for replenishing said depleted nasal spray with a diluent, wherein when said spray is depleted to said pre-selected level, said diluent is added to replenish the volume to said initial level of said spray.

17. The apparatus of claim 16, wherein said at least one indicia is located at the level of 85% of the initial volume of spray.

18. The apparatus of claim 17, further comprising a second indicia on said container showing the initial level of said spray in said container.

19. The apparatus of claim 18, wherein said diluent is sodium chloride solution.

20. The apparatus of claim 19, wherein said container has a screw-off top for ease in adding diluent.

* * * * *

UNITED STATES PATENT AND TRADEMARK OFFICE
CERTIFICATE OF CORRRECTION

PATENT NO. : 5,988,870
DATED : November 23, 1999
INVENTOR(S) : Howard Partsky Page 1 of 2

It is certified that error appears in the above-identified patent and that said Letters Patent is hereby corrected as shown below:

On the title page, item [56] add the following:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 3 | 8 | 8 | 5 | 0 | 2 | 7 | 5/20/75 | Shaw, et al. | | | |
| | | 4 | 4 | 9 | 6 | 5 | 4 | 5 | 1/29/85 | Scherschlicht, et al. | | | |
| | | 4 | 5 | 0 | 0 | 5 | 1 | 5 | 2/19/85 | Libby | | | |
| | | 4 | 5 | 8 | 2 | 7 | 0 | 5 | 4/15/86 | Primes, et al. | | | |
| | | 4 | 5 | 9 | 6 | 8 | 2 | 5 | 6/24/86 | Suda, et al. | | | |
| | | 4 | 9 | 7 | 0 | 2 | 4 | 0 | 11/13/90 | Kielley | | | |
| | | 5 | 1 | 1 | 4 | 9 | 7 | 9 | 5/19/92 | Kielley | | | |
| | | 5 | 1 | 9 | 8 | 2 | 3 | 0 | 3/30/93 | Wen | | | |
| | | 5 | 2 | 1 | 9 | 8 | 5 | 8 | 6/15/93 | Parnell | | | |
| | | 5 | 2 | 7 | 2 | 1 | 4 | 9 | 12/21/93 | Stalling | | | |
| | | 5 | 6 | 5 | 6 | 2 | 5 | 5 | 8/12/97 | Jones | | | |
| | | 5 | 6 | 8 | 8 | 8 | 0 | 4 | 11/18/97 | Rosen | | | |
| | | 5 | 5 | 9 | 4 | 0 | 3 | 0 | 1/14/97 | Conte et al. | | | |

UNITED STATES PATENT AND TRADEMARK OFFICE
CERTIFICATE OF CORRRECTION

PATENT NO. : 5,988,870
DATED : November 23, 1999
INVENTOR(S) : Howard Partsky It is certified that error appears in the above-identified patent and that said Letters Patent is hereby corrected as shown below:

OTHER DOCUMENTS(Including Author, Title, Date, Pertinent Page, Etc.)

Peter Graf, "Ocersue of Oxy-and Xylometazoline Nasal Sprays", Dept. of Otorhinolaryngology, Soder Hospital, Karolinska Institute, Stockholm, Sweden. ISBN91-628-1395-1, 1994

In section [19], the name should read  Paritsky .

In section [76], the inventor name should read, Howard Paritsky.

Signed and Sealed this

Twenty-fifth Day of July, 2000

*Attest:*

Q. TODD DICKINSON

*Attesting Officer*     *Director of Patents and Trademarks*